(12) United States Patent
Morriss et al.

(10) Patent No.: US 11,202,644 B2
(45) Date of Patent: Dec. 21, 2021

(54) SHAPEABLE GUIDE CATHETERS AND RELATED METHODS

(71) Applicant: Acclarent, Inc., Irvine, CA (US)

(72) Inventors: John H. Morriss, Emerald Hills, CA (US); Mei Y. Pader, Fremont, CA (US)

(73) Assignee: Acclarent, Inc., Irvine, CA (US)

( * ) Notice: Subject to any disclaimer, the term of this patent is extended or adjusted under 35 U.S.C. 154(b) by 870 days.

(21) Appl. No.: 15/624,093

(22) Filed: Jun. 15, 2017

(65) Prior Publication Data

US 2017/0340340 A1 Nov. 30, 2017

Related U.S. Application Data

(63) Continuation of application No. 14/265,888, filed on Apr. 30, 2014, now Pat. No. 9,700,326, which is a (Continued)

(51) Int. Cl.
*A61M 25/00* (2006.01)
*A61B 17/16* (2006.01)
(Continued)

(52) U.S. Cl.
CPC .......... *A61B 17/1657* (2013.01); *A61B 17/24* (2013.01); *A61B 17/32002* (2013.01);
(Continued)

(58) Field of Classification Search
CPC .............. A61B 17/24; A61B 2017/003; A61B 2017/3486; A61M 25/0053;
(Continued)

(56) References Cited

U.S. PATENT DOCUMENTS 446,173 A 2/1891 Hancock
504,424 A 9/1893 De Pezzer
(Continued)

FOREIGN PATENT DOCUMENTS

CA 2013323 9/1990
CH 668188 12/1988
(Continued)

OTHER PUBLICATIONS

Strohm et al. Die Behandlung von Stenosen der oberen Luftwege mittels rontgenologisch gesteuerter, Ballondilation Sep. 1999 ("Strohm"). (Year: 1999).*

(Continued)

*Primary Examiner* — Deanna K Hall
(74) *Attorney, Agent, or Firm* — Frost Brown Todd LLC

(57) ABSTRACT

Shapeable guide catheters and methods for manufacturing and using such shapeable guide catheters. In one embodiment, the shapeable guide catheter comprises a tubular member having a shapeable region, a malleable shaping member attached to the shapeable region such that, when the shape of the shapeable region is changed from a first shape to a second shape, the shaping member will plastically deform to thereafter substantially hold the shapeable region in the second shape, a tubular outer jacket disposed about the outer surface of the tubular member and a tubular inner jacket disposed within the lumen of the tubular member. The shapeable region of the guide catheter may be manually formed into a desired shape before insertion of the guide catheter into the body. In some embodiments, the guide catheter is sized to be inserted through a nostril of a human patient and used to guide the transnasal insertion of another device (e.g., a guidewire, catheter, etc.) to a desired location within the nose, throat, ear or cranium of the subject.

19 Claims, 7 Drawing Sheets

Related U.S. Application Data continuation of application No. 11/804,309, filed on May 16, 2007, now Pat. No. 8,932,276, which is a continuation-in-part of application No. 11/150,847, filed on Jun. 10, 2005, now Pat. No. 7,803,150, which is a continuation-in-part of application No. 11/037,548, filed on Jan. 18, 2005, now Pat. No. 7,462,175, which is a continuation-in-part of application No. 10/944,270, filed on Sep. 17, 2004, now abandoned, which is a continuation-in-part of application No. 10/912,578, filed on Aug. 4, 2004, now Pat. No. 7,361,168, which is a continuation-in-part of application No. 10/829,917, filed on Apr. 21, 2004, now Pat. No. 7,654,997.

(51) Int. Cl.
| | |
|---|---|
| *A61B 17/24* | (2006.01) |
| *A61B 17/32* | (2006.01) |
| *A61B 17/3207* | (2006.01) |
| *A61M 25/06* | (2006.01) |
| *A61M 25/10* | (2013.01) |
| *A61B 17/88* | (2006.01) |
| *A61B 90/16* | (2016.01) |
| *A61B 34/20* | (2016.01) |
| *A61B 10/06* | (2006.01) |
| *A61B 17/34* | (2006.01) |
| *A61B 17/00* | (2006.01) |
| *A61B 18/00* | (2006.01) |
| *A61B 90/00* | (2016.01) |

(52) U.S. Cl.
CPC .... *A61B 17/32075* (2013.01); *A61B 17/8866* (2013.01); *A61B 34/20* (2016.02); *A61B 90/16* (2016.02); *A61M 25/0012* (2013.01); *A61M 25/0041* (2013.01); *A61M 25/0662* (2013.01); *A61M 25/10* (2013.01); *A61B 10/06* (2013.01); *A61B 17/3478* (2013.01); *A61B 90/361* (2016.02); *A61B 2017/003* (2013.01); *A61B 2017/00526* (2013.01); *A61B 2017/00946* (2013.01); *A61B 2017/320004* (2013.01); *A61B 2017/3486* (2013.01); *A61B 2017/3488* (2013.01); *A61B 2018/00392* (2013.01); *A61B 2034/2051* (2016.02); *A61M 25/007* (2013.01); *A61M 25/0053* (2013.01); *A61M 25/0054* (2013.01); *A61M 2025/105* (2013.01); *A61M 2025/1052* (2013.01)

(58) Field of Classification Search
CPC .......... A61M 25/0054; A61M 25/0662; A61M 25/10; A61M 25/0013
See application file for complete search history.

(56) References Cited

U.S. PATENT DOCUMENTS

| | | | |
|---|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,137 A | 6/1970 | Santomieri |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,311,146 A | 1/1982 | Wonder |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,441,495 A | 4/1984 | Hicswa |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,517,979 A | 5/1985 | Pecenka |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |

(56) References Cited

U.S. PATENT DOCUMENTS

| | | |
|---|---|---|
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,592,357 A | 6/1986 | Ersek |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,641,654 A | 2/1987 | Samson et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,682,607 A | 7/1987 | Vaillancourt et al. |
| 4,691,948 A | 9/1987 | Austin, Jr. et al. |
| 4,696,544 A | 9/1987 | Costella |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,753,637 A | 6/1988 | Horneffer |
| 4,755,171 A | 7/1988 | Tennant |
| 4,771,776 A | 9/1988 | Powell et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,834,709 A | 5/1989 | Banning et al. |
| 4,846,186 A | 7/1989 | Box et al. |
| 4,847,258 A | 7/1989 | Sturm et al. |
| 4,851,228 A | 7/1989 | Zenter et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,953,553 A | 9/1990 | Tremulis |
| 4,961,433 A | 10/1990 | Christian |
| 4,966,163 A | 10/1990 | Kraus et al. |
| 4,984,581 A | 1/1991 | Stice |
| 4,986,810 A | 1/1991 | Semrad |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,040,548 A | 8/1991 | Yock |
| 5,041,089 A | 8/1991 | Mueller et al. |
| 5,044,678 A | 9/1991 | Detweiler |
| 5,049,132 A | 9/1991 | Shaffer et al. |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,099,845 A | 3/1992 | Besz et al. |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,161,534 A | 11/1992 | Berthiaume |
| 5,163,989 A | 11/1992 | Campbell et al. |
| 5,167,220 A | 12/1992 | Brown |
| 5,168,864 A | 12/1992 | Skockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,195,971 A | 3/1993 | Sirhan |
| 5,197,457 A | 3/1993 | Adair |
| 5,207,695 A | 5/1993 | Trout, III |
| 5,211,952 A | 5/1993 | Spicer et al. |
| 5,213,576 A | 5/1993 | Abiuso et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,306,272 A | 4/1994 | Cohen et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |

(56) References Cited

U.S. PATENT DOCUMENTS

| | | |
|---|---|---|
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,370,640 A | 12/1994 | Koloff |
| 5,372,138 A | 12/1994 | Crowley et al. |
| 5,372,584 A | 12/1994 | Zink et al. |
| D355,031 S | 1/1995 | Yoshikawa |
| 5,385,562 A | 1/1995 | Adams et al. |
| 5,386,817 A | 2/1995 | Jones |
| 5,386,828 A | 2/1995 | Owens et al. |
| 5,391,147 A | 2/1995 | Imran et al. |
| 5,391,179 A | 2/1995 | Mezzoli |
| 5,395,367 A | 3/1995 | Wilk |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,653,690 A | 8/1997 | Booth et al. |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,720,719 A | 2/1998 | Edwards et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,749,357 A | 5/1998 | Linder |
| 5,752,513 A | 5/1998 | Acker et al. |
| 5,752,971 A | 5/1998 | Rosenbluth et al. |
| 5,762,604 A | 6/1998 | Kieturakis |
| 5,766,158 A | 6/1998 | Opolski |
| 5,769,821 A | 6/1998 | Abrahamson et al. |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,824,044 A | 10/1998 | Quiachon et al. |
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,836,951 A | 11/1998 | Rosenbluth et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,882,333 A | 3/1999 | Schaer et al. |
| 5,882,346 A | 3/1999 | Pomeranz et al. |

(56) References Cited

U.S. PATENT DOCUMENTS

| | | |
|---|---|---|
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,967,984 A | 10/1999 | Chu et al. |
| 5,968,085 A | 10/1999 | Morris et al. |
| 5,971,975 A | 10/1999 | Mills et al. |
| 5,976,074 A | 11/1999 | Moriyama |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,993,462 A | 11/1999 | Pomeranz et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,022 A | 5/2000 | Ben-Haim |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,776 B1 | 1/2001 | Adams et al. |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,248,092 B1 | 6/2001 | Miraki et al. |
| 6,249,180 B1 | 6/2001 | Maalej et al. |
| 6,254,550 B1 | 7/2001 | McNamara et al. |
| 6,268,574 B1 | 7/2001 | Edens |
| 6,270,477 B1 | 8/2001 | Bagaoisan et al. |
| 6,280,433 B1 | 8/2001 | McIvor et al. |
| 6,283,908 B1 | 9/2001 | Powell et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,304,768 B1 | 10/2001 | Blume et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,328,730 B1 | 12/2001 | Harkrider, Jr. |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,379,319 B1 | 4/2002 | Garibotto et al. |
| 6,381,485 B1 | 4/2002 | Hunter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,436,119 B1 | 8/2002 | Erb et al. |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |

(56) References Cited

U.S. PATENT DOCUMENTS

| | | |
|---|---|---|
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,520,954 B2 | 2/2003 | Ouchi |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,562,022 B2 | 5/2003 | Hoste et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,833 B2 | 1/2004 | Smith et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,755,812 B2 | 6/2004 | Peterson et al. |
| 6,758,857 B2 | 7/2004 | Cioanta et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovegno |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,979,979 B2 | 12/2005 | Xu et al. |
| 6,984,203 B2 | 1/2006 | Tartaglia et al. |
| 6,989,024 B2 | 1/2006 | Hebert et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,004,176 B2 | 2/2006 | Lau |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,044,964 B2 | 5/2006 | Jang et al. |
| 7,048,711 B2 | 5/2006 | Rosenman et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 * | 11/2006 | Hovda ............... A61B 18/1402 606/45 |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,186,224 B2 | 3/2007 | Windheuser |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,248,914 B2 | 7/2007 | Hastings et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |

(56) References Cited

U.S. PATENT DOCUMENTS

| | | | |
|---|---|---|---|
| 7,294,365 | B2 | 11/2007 | Hayakawa et al. |
| 7,303,533 | B2 | 12/2007 | Johansen et al. |
| 7,313,430 | B2 | 12/2007 | Urquhart et al. |
| 7,316,168 | B2 | 1/2008 | van der Knokke et al. |
| 7,316,656 | B2 | 1/2008 | Shireman et al. |
| 7,318,831 | B2 | 1/2008 | Alvarez et al. |
| 7,322,934 | B2 | 1/2008 | Miyake et al. |
| 7,326,235 | B2 | 2/2008 | Edwards |
| 7,338,467 | B2 | 3/2008 | Lutter |
| 7,343,920 | B2 | 3/2008 | Toby et al. |
| 7,347,868 | B2 | 3/2008 | Burnett et al. |
| 7,359,755 | B2 | 4/2008 | Jones et al. |
| 7,361,168 | B2 | 4/2008 | Makower et al. |
| 7,366,562 | B2 | 4/2008 | Dukesherer |
| 7,371,210 | B2 | 5/2008 | Brock et al. |
| 7,381,205 | B2 | 6/2008 | Thommen |
| 7,410,480 | B2 | 8/2008 | Muni et al. |
| 7,419,497 | B2 | 9/2008 | Muni et al. |
| 7,438,701 | B2 | 10/2008 | Theeuwes et al. |
| 7,442,191 | B2 | 10/2008 | Hovda et al. |
| 7,452,351 | B2 | 11/2008 | Miller et al. |
| 7,454,244 | B2 | 11/2008 | Kassab et al. |
| 7,462,175 | B2 | 12/2008 | Chang et al. |
| 7,471,994 | B2 | 12/2008 | Ford et al. |
| 7,481,218 | B2 | 1/2009 | Djupesland |
| 7,481,800 | B2 | 1/2009 | Jacques |
| D586,465 | S | 2/2009 | Faulkner et al. |
| D586,916 | S | 2/2009 | Faulkner et al. |
| 7,488,313 | B2 | 2/2009 | Segal et al. |
| 7,488,337 | B2 | 2/2009 | Saab et al. |
| 7,493,156 | B2 | 2/2009 | Manning et al. |
| 7,497,844 | B2 * | 3/2009 | Spear .......... A61M 25/008 604/164.01 |
| 7,500,971 | B2 | 3/2009 | Chang et al. |
| D590,502 | S | 4/2009 | Geisser et al. |
| 7,520,876 | B2 | 4/2009 | Ressemann et al. |
| 7,532,920 | B1 | 5/2009 | Ainsworth et al. |
| 7,544,192 | B2 | 6/2009 | Eaton et al. |
| 7,559,925 | B2 | 7/2009 | Goldfarb et al. |
| 7,566,300 | B2 | 7/2009 | Devierre et al. |
| 7,610,104 | B2 | 10/2009 | Kaplan et al. |
| 7,615,005 | B2 | 11/2009 | Stefanchik et al. |
| 7,618,450 | B2 | 11/2009 | Zarowski et al. |
| 7,625,335 | B2 | 12/2009 | Deichmann et al. |
| 7,632,291 | B2 | 12/2009 | Stephens et al. |
| 7,634,233 | B2 | 12/2009 | Deng et al. |
| 7,641,644 | B2 | 1/2010 | Chang et al. |
| 7,641,668 | B2 | 1/2010 | Perry et al. |
| 7,645,272 | B2 | 1/2010 | Chang et al. |
| 7,648,367 | B1 | 1/2010 | Makower et al. |
| 7,654,997 | B2 | 2/2010 | Makower et al. |
| 7,680,244 | B2 | 3/2010 | Gertner et al. |
| 7,686,798 | B2 | 3/2010 | Eaton et al. |
| 7,691,120 | B2 | 4/2010 | Shluzas et al. |
| 7,697,972 | B2 | 4/2010 | Verard et al. |
| 7,717,933 | B2 | 5/2010 | Becker |
| 7,720,521 | B2 | 5/2010 | Chang et al. |
| 7,727,186 | B2 | 6/2010 | Makower et al. |
| 7,727,226 | B2 | 6/2010 | Chang et al. |
| 7,736,301 | B1 | 6/2010 | Webler et al. |
| 7,740,642 | B2 | 6/2010 | Becker |
| 7,753,929 | B2 | 7/2010 | Becker |
| 7,753,930 | B2 | 7/2010 | Becker |
| 7,771,409 | B2 | 8/2010 | Chang et al. |
| 7,775,968 | B2 | 8/2010 | Mathis |
| 7,785,315 | B1 | 8/2010 | Muni et al. |
| 7,799,048 | B2 | 9/2010 | Hudson et al. |
| 7,799,337 | B2 | 9/2010 | Levin |
| 7,803,150 | B2 | 9/2010 | Chang et al. |
| 7,833,282 | B2 | 11/2010 | Mandpe |
| 7,837,672 | B2 | 11/2010 | Intoccia |
| 7,840,254 | B2 | 11/2010 | Glossop |
| 7,854,744 | B2 | 12/2010 | Becker |
| 7,857,750 | B2 | 12/2010 | Belafsky |
| D630,321 | S | 1/2011 | Hamilton, Jr. |
| 7,875,050 | B2 | 1/2011 | Samson et al. |
| D632,791 | S | 2/2011 | Murner |
| 7,881,769 | B2 | 2/2011 | Sobe |
| 7,883,717 | B2 | 2/2011 | Varner et al. |
| 7,896,891 | B2 | 3/2011 | Catanese, III et al. |
| 7,927,271 | B2 | 4/2011 | Dimitriou et al. |
| 7,951,132 | B2 | 5/2011 | Eaton et al. |
| 7,988,705 | B2 | 8/2011 | Galdonik et al. |
| 7,993,353 | B2 | 8/2011 | Roβner et al. |
| 8,002,740 | B2 | 8/2011 | Willink et al. |
| 8,014,849 | B2 | 9/2011 | Peckham |
| 8,016,752 | B2 | 9/2011 | Armstrong et al. |
| 8,025,635 | B2 | 9/2011 | Eaton et al. |
| 8,075,476 | B2 | 12/2011 | Vargas |
| 8,080,000 | B2 | 12/2011 | Makower et al. |
| 8,088,063 | B2 | 1/2012 | Fujikura et al. |
| 8,088,101 | B2 | 1/2012 | Chang et al. |
| 8,090,433 | B2 | 1/2012 | Makower et al. |
| 8,100,933 | B2 | 1/2012 | Becker |
| 8,104,483 | B2 | 1/2012 | Taylor |
| 8,114,062 | B2 | 2/2012 | Muni et al. |
| 8,114,113 | B2 | 2/2012 | Becker |
| 8,123,722 | B2 | 2/2012 | Chang et al. |
| 8,142,422 | B2 | 3/2012 | Makower et al. |
| 8,146,400 | B2 | 4/2012 | Goldfarb et al. |
| 8,147,545 | B2 | 4/2012 | Avior |
| 8,167,821 | B2 | 5/2012 | Sharrow |
| 8,172,828 | B2 | 5/2012 | Chang et al. |
| 8,190,389 | B2 | 5/2012 | Kim et al. |
| 8,197,433 | B2 | 6/2012 | Cohen |
| 8,197,552 | B2 | 6/2012 | Mandpe |
| 8,249,700 | B2 | 8/2012 | Clifford et al. |
| 8,277,386 | B2 | 10/2012 | Ahmed et al. |
| 8,317,816 | B2 | 11/2012 | Becker |
| 8,337,454 | B2 | 12/2012 | Eaton et al. |
| 8,388,642 | B2 | 3/2013 | Muni et al. |
| 8,403,954 | B2 | 3/2013 | Santin et al. |
| 8,414,473 | B2 | 4/2013 | Jenkins et al. |
| 8,425,457 | B2 | 4/2013 | John et al. |
| 8,439,687 | B1 | 5/2013 | Morriss et al. |
| 8,475,360 | B2 | 7/2013 | Brown |
| 8,529,439 | B2 | 9/2013 | Ito et al. |
| 8,535,707 | B2 | 9/2013 | Arensdorf et al. |
| 8,702,626 | B1 | 4/2014 | Kim et al. |
| 8,715,169 | B2 | 5/2014 | Chang et al. |
| 8,721,591 | B2 | 5/2014 | Chang et al. |
| 8,747,389 | B2 | 6/2014 | Goldfarb et al. |
| 8,764,709 | B2 | 7/2014 | Chang et al. |
| 8,764,726 | B2 | 7/2014 | Chang et al. |
| 8,764,729 | B2 | 7/2014 | Muni et al. |
| 8,777,926 | B2 | 7/2014 | Chang et al. |
| 8,828,041 | B2 | 9/2014 | Chang et al. |
| 2001/0004644 | A1 | 6/2001 | Levin |
| 2001/0005785 | A1 | 6/2001 | Sachse |
| 2001/0034530 | A1 | 10/2001 | Malackowski et al. |
| 2002/0006961 | A1 | 1/2002 | Katz et al. |
| 2002/0055746 | A1 | 5/2002 | Burke et al. |
| 2002/0068851 | A1 | 6/2002 | Gravenstein et al. |
| 2002/0077593 | A1 | 6/2002 | Perkins et al. |
| 2002/0090388 | A1 | 7/2002 | Humes et al. |
| 2002/0115963 | A1 | 8/2002 | Clarke et al. |
| 2003/0013985 | A1 | 1/2003 | Saadat |
| 2003/0017111 | A1 | 1/2003 | Rabito |
| 2003/0018291 | A1 | 1/2003 | Hill et al. |
| 2003/0040697 | A1 | 2/2003 | Pass et al. |
| 2003/0069522 | A1 * | 4/2003 | Jacobsen .......... A61M 25/0013 600/585 |
| 2003/0073900 | A1 | 4/2003 | Senarith et al. |
| 2003/0083608 | A1 | 5/2003 | Evans et al. |
| 2003/0114732 | A1 | 6/2003 | Webler et al. |
| 2003/0163154 | A1 | 8/2003 | Miyata et al. |
| 2003/0220551 | A1 | 11/2003 | Kimball et al. |
| 2004/0015150 | A1 | 1/2004 | Zadno-Azizi |
| 2004/0018980 | A1 | 1/2004 | Gurney et al. |
| 2004/0020492 | A1 | 2/2004 | Dubrul et al. |
| 2004/0034311 | A1 | 2/2004 | Mihakcik |
| 2004/0043052 | A1 | 3/2004 | Hunter et al. |
| 2004/0058992 | A1 | 3/2004 | Marinello et al. |
| 2004/0064105 | A1 | 4/2004 | Capes et al. |

(56) References Cited

U.S. PATENT DOCUMENTS

| | | |
|---|---|---|
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0220470 A1* | 11/2004 | Karmarkar ............ G01R 33/287 600/423 |
| 2004/0220516 A1 | 11/2004 | Solomon et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0038319 A1 | 2/2005 | Goldwasser et al. |
| 2005/0055077 A1 | 3/2005 | Marco |
| 2005/0059930 A1 | 3/2005 | Garrison et al. |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228224 A1 | 10/2005 | Okada et al. |
| 2005/0234507 A1 | 10/2005 | Geske et al. |
| 2005/0240120 A1 | 10/2005 | Modesitt |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0250105 A1 | 10/2007 | Ressemann et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0172033 A1 | 7/2008 | Keith et al. |
| 2008/0183128 A1 | 7/2008 | Morriss et al. |
| 2008/0188803 A1 | 8/2008 | Jang |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0211007 A1 | 8/2010 | Lesch, Jr. et al. |
| 2010/0268245 A1 | 10/2010 | Chang et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | John et al. |
| 2013/0245608 A1 | 9/2013 | Muni et al. |
| 2013/0261388 A1 | 10/2013 | Jenkins et al. |

FOREIGN PATENT DOCUMENTS

| | | |
|---|---|---|
| CN | 2151720 | 1/1994 |
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1166710 | 1/2002 |
| EP | 1413258 | 4/2004 |
| EP | 1944053 | 7/2008 |
| FR | 2662083 | 11/1991 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 10-034376 | 2/1989 |
| JP | 3-503011 | 7/1991 |
| JP | 3-504935 | 10/1991 |
| JP | 4-221313 | 8/1992 |
| JP | 4-224766 | 8/1992 |

(56) References Cited

FOREIGN PATENT DOCUMENTS

| | | |
|---|---|---|
| JP | H5-503650 | 6/1993 |
| JP | 5-211985 | 8/1993 |
| JP | 06-17751 | 3/1994 |
| JP | 6-277296 | 10/1994 |
| JP | 7-327916 | 12/1995 |
| JP | 8-317989 | 12/1996 |
| JP | H10-94543 | 4/1998 |
| JP | 11-507251 | 6/1999 |
| JP | 2000-501634 | 2/2000 |
| JP | 2000-126303 | 5/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 2004-357728 | 12/2004 |
| JP | 2005-323702 | 11/2005 |
| JP | 2005-532869 | 11/2005 |
| JP | 2008-539031 | 11/2008 |
| RU | 2108764 | 4/1998 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 94/021320 | 9/1994 |
| WO | WO 95/002430 | 1/1995 |
| WO | WO 96/029071 | 9/1996 |
| WO | WO 97/021461 | 6/1997 |
| WO | WO 98/055174 | 12/1998 |
| WO | WO 99/000064 | 1/1999 |
| WO | WO 99/024106 | 5/1999 |
| WO | WO 99/026692 | 6/1999 |
| WO | WO 99/030655 | 6/1999 |
| WO | WO 99/032041 | 7/1999 |
| WO | WO 99/059649 | 11/1999 |
| WO | WO 00/009190 | 2/2000 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 00/067834 | 11/2000 |
| WO | WO 01/005462 | 1/2001 |
| WO | WO 01/045572 | 6/2001 |
| WO | WO 01/054558 | 8/2001 |
| WO | WO 01/056481 | 8/2001 |
| WO | WO 01/068178 | 9/2001 |
| WO | WO 01/070325 | 9/2001 |
| WO | WO 01/074266 | 10/2001 |
| WO | WO 01/097895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/045387 | 6/2004 |
| WO | WO 04/058045 | 7/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/034203 | 3/2007 |
| WO | WO 07/035204 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

Supplemental European Search Report dated Sep. 8, 2011 for Application No. EP 06800540.4.
Extended European Search Report dated Jun. 28, 2017 for Application No. EP 17159646.3.
U.S. Appl. No. 10/912,557.
U.S. Appl. No. 10/944,270.
U.S. Appl. No. 11/193,020.
U.S. Appl. No. 11/355,512.
U.S. Appl. No. 11/436,892.
U.S. Appl. No. 11/438,090.
U.S. Appl. No. 11/647,530.
U.S. Appl. No. 11/648,158.
U.S. Appl. No. 11/655,794.
U.S. Appl. No. 11/725,151.
U.S. Appl. No. 11/789,704.
U.S. Appl. No. 11/789,705.
U.S. Appl. No. 11/803,695.
U.S. Appl. No. 11/804,308.
U.S. Appl. No. 11/804,309.
U.S. Appl. No. 11/888,284.
U.S. Appl. No. 11/926,565.
U.S. Appl. No. 11/928,097.
U.S. Appl. No. 11/929,667.
U.S. Appl. No. 11/929,808.
U.S. Appl. No. 11/930,716.
U.S. Appl. No. 11/930,786.
U.S. Appl. No. 12/100,361.
U.S. Appl. No. 12/143,698.
U.S. Appl. No. 12/184,166.
U.S. Appl. No. 12/341,602.
U.S. Appl. No. 12/496,226.
U.S. Appl. No. 12/543,445.
U.S. Appl. No. 12/639,919.
U.S. Appl. No. 12/649,027.
U.S. Appl. No. 12/727,190.
U.S. Appl. No. 12/729,109.
U.S. Appl. No. 12/768,963.
U.S. Appl. No. 12/769,915.
U.S. Appl. No. 12/793,352.
U.S. Appl. No. 12/828,170.
U.S. Appl. No. 12/949,708.
U.S. Appl. No. 13/301,406.
U.S. Appl. No. 13/315,191.
U.S. Appl. No. 13/355,758.
U.S. Appl. No. 13/429,857.
U.S. Appl. No. 13/451,453.
U.S. Appl. No. 13/784,293.
U.S. Appl. No. 13/840,430.
U.S. Appl. No. 13/858,580.
U.S. Appl. No. 13/867,972.
U.S. Appl. No. 14/221,550.
U.S. Appl. No. 14/221,621.
U.S. Appl. No. 14/221,714.
U.S. Appl. No. 14/265,787.
U.S. Appl. No. 14/265,888.
U.S. Appl. No. 14/266,002.

(56) References Cited

OTHER PUBLICATIONS

U.S. Appl. No. 14/266,025.
U.S. Appl. No. 14/327,593.
U.S. Appl. No. 14/464,948.
U.S. Appl. No. 14/515,687.
U.S. Appl. No. 15/595,319.
Argon Medical. Maxxim Medical. Ad for Sniper EliteTM Hydrophilic Ni—Ti Alloy Guidewire (2001).
Aust, R., et al. 'The Functional Size of the Human Maxillary Ostium in Vivo' Acta. Otolaryn. (9178) vol. 78 pp. 432-435, no date given.
Baim, D.S., Md 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congential Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. Www.inventors.about.com/library/inventors/blcatheter.htm?p=1, no date given.
Benninger et al.; Adult Chronic Rhinosinusitis: Defintions, Diagnosis, Epidemiology, and Pathophysilogy Arch Otolaryogl Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: the University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, pp. 60-63, no date given.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers-General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.

ENT Checklist: Physical Examination Performance Checklist [date of publication unknown], no date given.
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence ot Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Front Sinus OASIS-Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substitutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound heal-

(56) References Cited

OTHER PUBLICATIONS ing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa. Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa In the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' Internatinal Advanced Sinus Symposium (1993) Jul. 21-24.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.

Medtronic, xomed.com-MicroFrance Catalog Browser. Www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html
Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Rhinology Products, Boston Medical Products, www.bosmed.com, [date of publication unknown], pp. 1-16, no date given.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' TEXAS State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown], no date given.

(56) References Cited

OTHER PUBLICATIONS

Shah. N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems, no date given.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischlieβ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitement Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn-Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4, no date given.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown], no date given.
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.
Australian Office Action, dated Feb. 12, 2014 for Application No. AU 2012202103.
Chinese Office Action, First Office Action dated Nov. 5, 2012 for CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for CN 200980152995.1.
European Communication dated Sep. 4, 2008 for Application No. EP 05773189.
European Communication dated Jun. 19, 2009 for Application No. EP 05773189.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Communication dated Sep. 27, 2011 for Application No. EP 06800540.4.
European Communication dated Sep. 3, 2013 for Application No. EP 12182998.0.
European Communication dated Feb. 26, 2014 for Application No. EP 06800540.4.
Extended European Search Report dated Jan. 17, 2014 for Application No. EP 108426321.1.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 re Application No. EP 06718986.
European Search Report dated Sep. 27, 2011 for Application No. EP 10182961.
European Search Report dated Sep. 29, 2011 for Application No. EP 10182893.
European Search Report dated Jul. 23, 2012 for Application No. EP 12162709.
European Search Report dated Jul. 24, 2012 for Application No. EP 12162712.
European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. EP 12183000.
European Search Report dated Jan. 11, 2013 for Application No. EP 12183002.

(56) References Cited

OTHER PUBLICATIONS

European Search Report dated Aug. 13, 2013 for Application No. EP 13172140.
European Search Report dated Sep. 9, 2013 for Application No. EP 13179223.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
Supplemental European Search Report dated Jan. 14, 2014 for Application No. EP 13184009.
Supplemental European Search Report dated Jan. 17, 2014 for Application No. EP 1084263.
Supplemental European Search Report dated Feb. 13, 2014 for Application No. EP 08746464.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
International Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.
International Search Report dated Aug. 25, 2008 for Application No. PCT/US2008/000911.
International Search Report dated Sep. 10, 2008 for Application No. PCT/US07/016212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.

(56) References Cited

OTHER PUBLICATIONS

Japanese Office Action, Notification of Reasons for Refusal dated Jun. 25, 2013 for Application No. JP 2012-131840.
Japanese Office Action, Notification of Reasons for Refusal dated Sep. 18, 2013 for Application No. JP 2011-527942.
Japanese Office Action, Notification of Reasons for Refusal dated Nov. 12, 2013 for Application No. JP 2011-542562.
Japanese Office Action, Notification of Reasons for Refusal dated Jan. 7, 2014 for Application No. JP 2012-266049.
Russian Office Action dated Sep. 28, 2012 for Application No. RU 2011130530.
Russian Office Action dated Mar. 19, 2013 for Application No. RU 2011130530.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 20, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 14/221,550, filed Mar. 21, 2014.
U.S. Appl. No. 14/221,621, filed Mar. 21, 2014.
U.S. Appl. No. 14/221,714, filed Mar. 21, 2014.
U.S. Appl. No. 14/265,787, filed Apr. 30, 2014.
U.S. Appl. No. 14/265,888, filed Apr. 20, 2014.
U.S. Appl. No. 14/266,002, filed Apr. 30, 2014.
U.S. Appl. No. 14/266,025, filed Apr. 30, 2014.
U.S. Appl. No. 14/327,593, filed Jul. 10, 2014.
U.S. Appl. No. 14/464,948, filed Aug. 21, 2014.
U.S. Appl. No. 15/595,319, filed May 15, 2017.

* cited by examiner

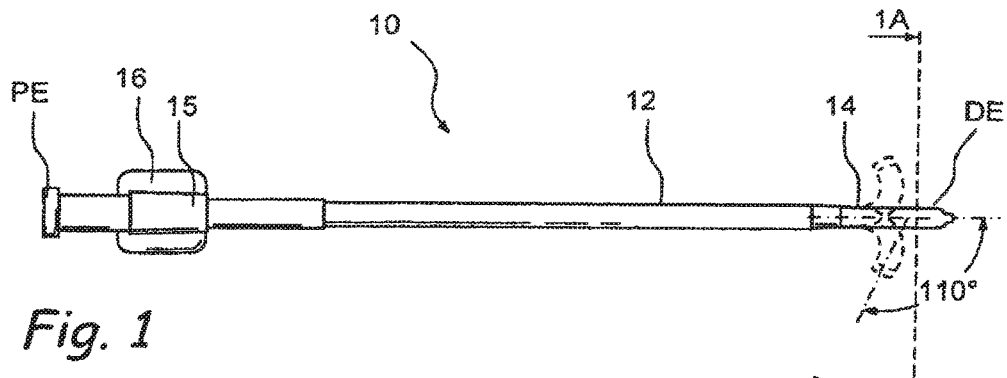
Fig. 1
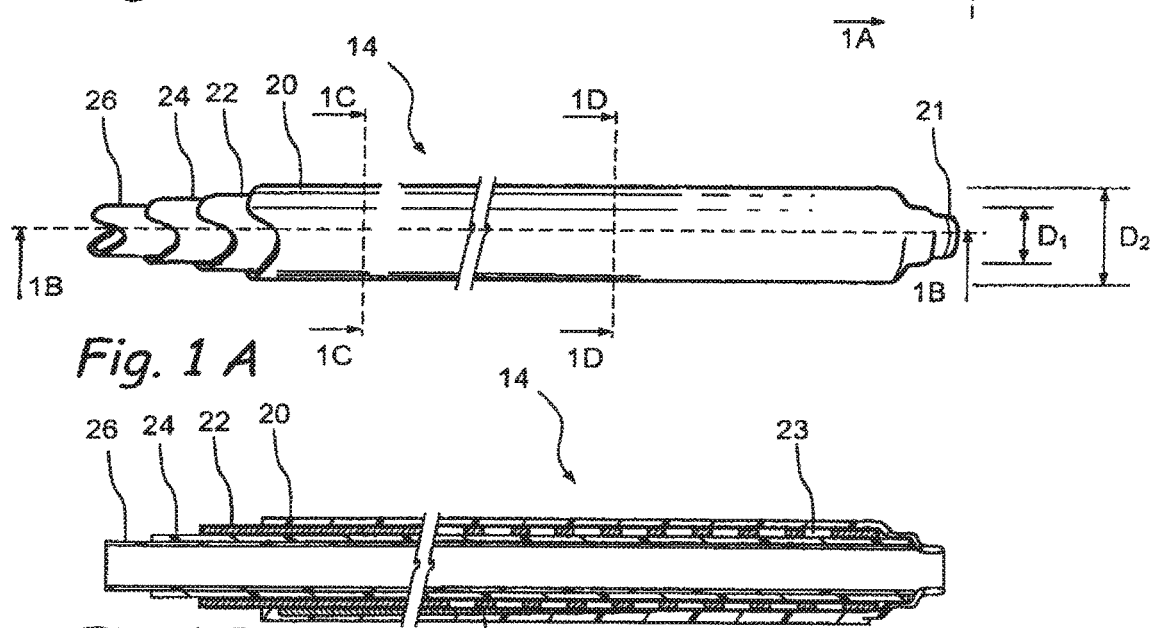
Fig. 1A
Fig. 1B
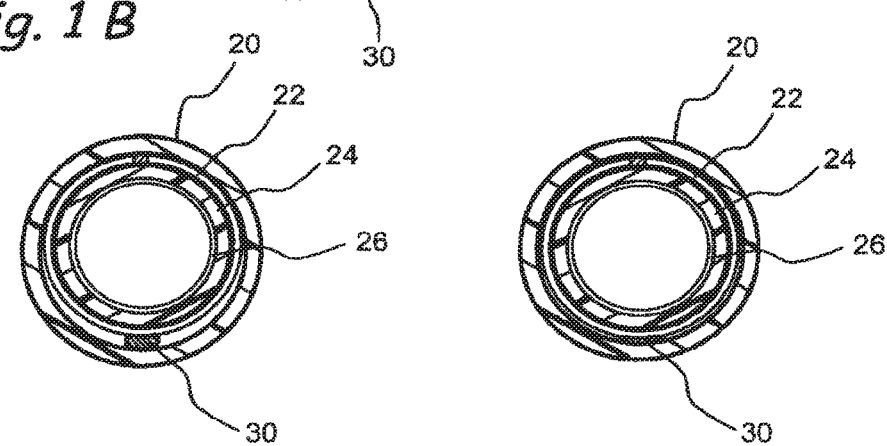
Fig. 1C    Fig. 1D

SHAPEABLE GUIDE CATHETERS AND RELATED METHODS

RELATED APPLICATIONS

This application is a continuation of U.S. patent application Ser. No. 14/265,888, entitled "Shapeable Guide Catheters and Related Methods," filed Apr. 30, 2014, now U.S. Pat. No. 9,700,326, which is a continuation of U.S. patent application Ser. No. 11/804,309, entitled "Shapeable Guide Catheters and Related Methods," filed May 16, 2007, now U.S. Pat. No. 8,932,276, which is a continuation in part of 1) U.S. patent application Ser. No. 11/037,548, entitled "Devices, Systems and Methods for Treating Disorders of the Ear, Nose and Throat," filed Jan. 18, 2005, now U.S. Pat. No. 7,462,175, which is a continuation in part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, now U.S. Pat. No. 7,654,997; 2) U.S. patent application Ser. No. 10/912,578, entitled "Implantable Device and Methods for Delivering Drugs and Other Substances to Treat Sinusitis and Other Disorders," filed on Aug. 4, 2004, now U.S. Pat. No. 7,361,168, which is a continuation in part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, now U.S. Pat. No. 7,654,997; 3) U.S. patent application Ser. No. 10/944,270, entitled "Apparatus and Methods for Dilating and Modifying Ostia of Paranasal Sinuses and Other Intranasal or Paranasal Structures," filed on Sep. 17, 2004, published as U.S. Pub. No. 2006/0004323, now abandoned, which is a continuation in part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, now U.S. Pat. No. 7,654,997, and 4) U.S. patent application Ser. No. 11/150,847, entitled Devices, Systems and Methods Useable for Treating Sinusitis," filed Jun. 10, 2005, now U.S. Pat. No. 7,803,150, which is a continuation in part of U.S. patent application Ser. No. 10/944,270, entitled "Apparatus and Methods for Dilating and Modifying Ostia of Paranasal Sinuses and Other Intranasal or Paranasal Structures," filed on Sep. 17, 2004, published as U.S. Pub. No. 2006/0004323, now abandoned, which is a continuation-in-part of U.S. patent application Ser. No. 10/829,917, entitled "Devices, Systems and Methods for Diagnosing and Treating Sinusitis and Other Disorders of the Ears, Nose and/or Throat," filed on Apr. 21, 2004, now U.S. Pat. No. 7,654,997, the entire disclosure of each such earlier-filed application being expressly incorporated herein by reference.

FIELD OF THE INVENTION

The present invention relates generally to medical apparatus and methods and more particularly to guide catheters that can be pre-shaped prior to insertion into a patient's body and their methods of manufacture and use.

BACKGROUND OF THE INVENTION

Various shapeable catheters have been known in the prior art. In some instances, a malleable element (e.g., a stylet or wire) is inserted into the lumen of a flexible catheter. The malleable element is either pre-shaped prior to insertion, or it is bent to a desired shape after it has been inserted into the catheter. In either event, the malleable element imparts a desired shape to the flexible catheter. In either instances, all or part of the catheter is formed of a malleable material that can be plastically deformed to a desired shape prior to or after insertion into a patient's body.

For example, U.S. Pat. No. 4,834,709 (Banning, et al.) describes a catheter and stylet assembly which includes a silicone rubber catheter and a malleable stylet. The stylet is formed of malleable metal covered by a plastic cover. The stylet is inserted into the catheter to permit the catheter to be manually shaped into a desired form before insertion into the patient. The stylet is removable from the catheter after the catheter has been inserted into the patient's body.

U.S. Pat. No. 5,720,719 (Edwards, et al.) describes an ablative catheter having a conshapeable body. The catheter's conshapeable body includes a malleable tube and a flexible tube that allow the catheter to conform to the curvature of a cavity inside a patient's body.

U.S. Pat. No. 5,749,357 (Linder) describes a malleable introducer tube that is useable to an endotracheal tube or the like. The introducer incorporates a malleable and shape-retaining tube along at least a portion of its length. In one embodiment, intermediation of the length between the sheath and the clamp is made almost entirely by a malleable tube made of a ductile metal such as aluminum. The tube may be thick-walled to reduce the volume necessary to inflate the sheath. In another embodiment, only the introducer tip may be of a malleable metal, such as copper. Significant advantages are offered by the use and inclusion of resilient, malleable portions in the introducer.

U.S. Pat. No. 5,882,346 describes a shapeable catheter and method for positioning such shapeable catheter within a body cavity. A core wire which includes a pre-shaped region is slidably received within a lumen of the catheter. The catheter includes a rigid proximal section and a flexible distal section. During use, the distal end of the catheter is inserted into a patient's vasculature and is passed into a body cavity. The pre-shaped region of the core wire is then passed into the lumen and is straightened by the rigid proximal section of the catheter. As the core wire is advanced into the more flexible distal region of the catheter, it re-assumes its predetermined shape and causes the core wire to form the distal section of the catheter into the predetermined shape. The distal section of the catheter is positioned in contact with tissue in the body cavity, and electrodes carried by the distal end are used to map and/or ablate the tissue.

U.S. Pat. No. 5,993,462 (Pomeranz, et al.) describes a shapeable catheter wherein a core wire is pre-shaped and slidably received within a lumen of the catheter. The catheter includes a rigid proximal section and a flexible distal section. A pull wire may additionally be provided to allow the user to cause deflection at a distal portion of the catheter.

U.S. Pat. No. 6,280,433 describes a tubular introducer or guide catheter for directing an implantable medical device such as a lead or catheter to a desired location within a patient's body. In one embodiment of the invention, the introducer comprises a two-lumen tube. A first lumen is configured to receive the implantable medical device that is to be introduced. A second lumen is provided to receive an insertable, elongated guiding member such as a stylet, which may be shapeable in various orientations, and which may be used to alter the configuration of the introducer. The second lumen may be provided with an internal coil or other tubular reinforcement member to prevent perforation of this lumen by the guiding member when the introducer is in the patient's body.

U.S. Pat. No. 6,979,979 (Lawrence, et al.) describes a malleable cannula. A reinforcement member extends along a lumen of the cannula, such reinforcement member having an interior side facing the lumen and an exterior side facing away from the lumen. A malleable member extends along a portion of the exterior side of the reinforcement member. The malleable member may be constructed of a tube with a wire slidably received within the tube and may include an anchor.

U.S. patent application Ser. No. 11/037,548, now U.S. Pat. No. 7,462,175, of which this is a continuation-in-part, describes malleable guide catheters that are useable to facilitate transnasal insertion of other devices (e.g., guidewires, balloon catheters, lavage catheters, etc.) into paranasal sinuses or other locations within the ear, nose or throat of a patient. Additionally, a system of transnasal guide catheters having malleable proximal shafts and pre-set distal curves of 0°, 30°, 70°, 90° and 110° are available commercially (Relieva® Sinus Guide Catheters, Acclarent, Inc., Menlo Park, Calif.).

There remains a need for further development of new guide catheters that may be pre-shaped prior to insertion into a patient's body and their methods of manufacture and use for transnasal and/or other applications.

SUMMARY OF THE INVENTION

In accordance with the present invention, there is provided a shapeable guide catheter device comprising a tubular member having (a) a shapeable region, (b) a malleable shaping member attached to the shapeable region such that, when the shape of the shapeable region is changed from a first shape to a second shape, the shaping member will plastically deform to and will thereafter substantially hold the shapeable region in such second shape, (c) a tubular outer jacket disposed about the outer surface of the tubular member and (d) a tubular inner jacket disposed within the lumen of the tubular member. In some embodiments the shapeable region may be created by forming one or more cut(s), groove(s), aperture(s) in, or otherwise weakening, a discrete region of the wall of the tubular member, thereby rendering that region more flexible than the remainder of the tubular member and thus defining the shapeable region of the device.

Further in accordance with the present invention, there is provided a method for positioning a device at a desired location within the ear, nose, throat or cranium of a human or animal subject, such method generally comprising the steps of (A) providing a shapeable guide catheter having a distal end, a lumen and a shapeable region that shapeable to a desired shape such that it will thereafter substantially retain that desired shape, (B) forming the shapeable region to a desired shape, (C) inserting the guide catheter, distal end first, through a nostril of the subject and advancing the guide catheter to a location at or near the desired location and (D) advancing the device through the lumen of the guide catheter and to or through the desired location.

Further aspects, elements and advantages of the present invention will be understood by those of skill in the art upon reading of the detailed description set forth herebelow.

BRIEF DESCRIPTION OF THE DRAWINGS

FIG. 1 is a side view of one embodiment of a malleable guide catheter of the present invention.

FIG. 1A is an enlarged, cut-away view of a distal portion of the guide catheter of FIG. 1.

FIG. 1B is a longitudinal sectional view through line 1B-1B of FIG. 1A.

FIG. 1C is a transverse sectional view through line 1C-1C of FIG. 1A.

FIG. 1D is a transverse sectional view through line 1 D-1 D of FIG. 1A.

FIG. 2B' is a transverse cross sectional view of a round wire before undergoing compression as illustrated in FIG. 2A.

FIG. 2B" is a transverse cross sectional view of the wire of FIG. 2B' after having undergone compression as illustrated in FIG. 2B.

DETAILED DESCRIPTION

Figure 2:
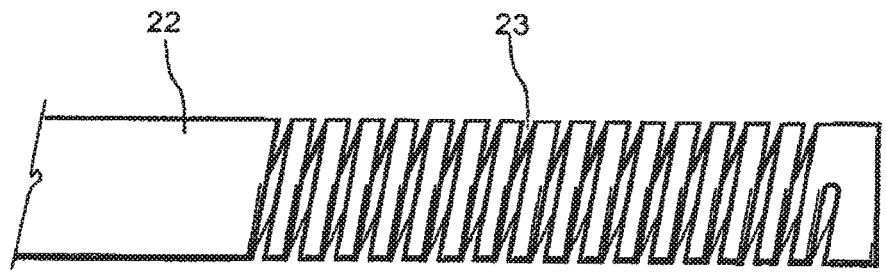
FIG. 2A is a side view of a helically cut tube component used in the manufacture of the malleable guide catheter of FIG. 1.
FIG. 2B is a schematic diagram showing an optional step in the manufacture of the malleable guide catheter of FIG. 1 wherein a shaping member component of the catheter is compressed from an initial round shape to a final non-round shape having flattened sides.
FIG. 2C is a side view of a helically cut tube component with one embodiment of a shaping member attached, as used in the manufacture of the malleable guide catheter of FIG. 1.
FIG. 2D is a partial view of the apparatus of FIG. 2C with the shaping member deformed to a curved shape.
FIG. 2E is a cross sectional view through line 2E-2E of FIG. 2D.
FIG. 2F is a cross sectional view through line 2F-2F of FIG. 2D.
FIG. 2G is a cross sectional view through line 2G-2G of FIG. 2D.
Figure 2:
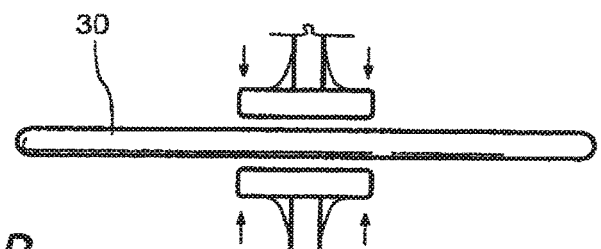
Figure 2:
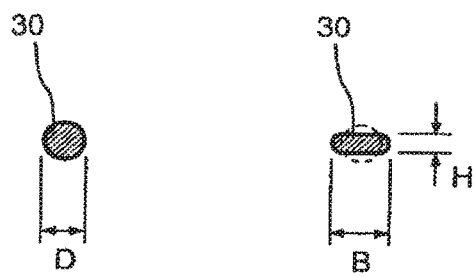
Figure 2:
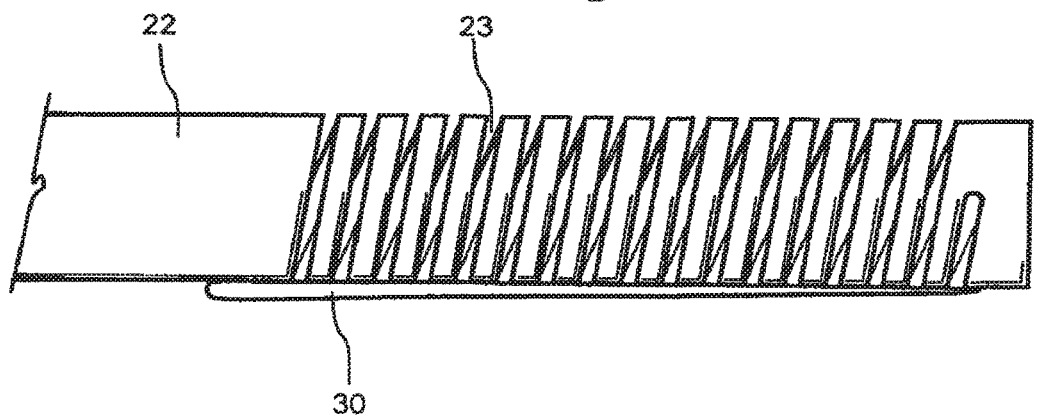
Figure 2:
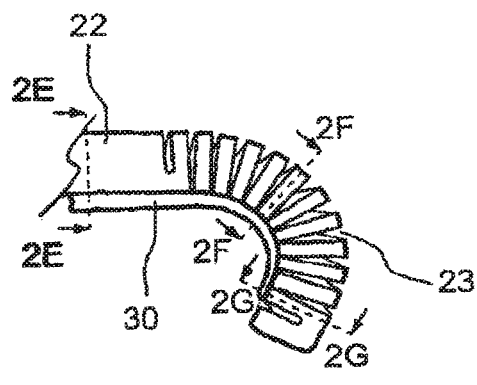
Figure 2:
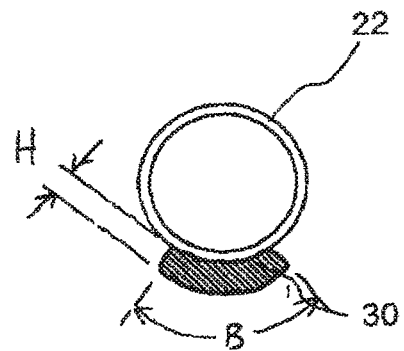
Figure 2:
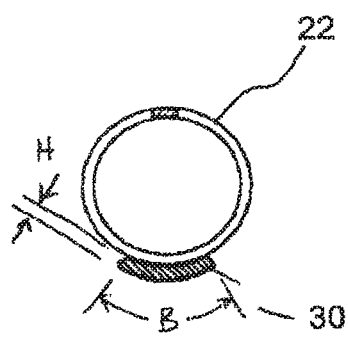
Figure 2:
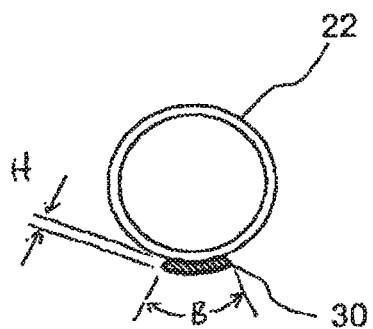

The following detailed description and the accompanying drawings are intended to describe some, but not necessarily all, examples or embodiments of the invention. The contents of this detailed description and the accompanying drawings do not limit the scope of the invention in any way.

FIG. 1 shows one embodiment of a shapeable guide catheter 10 of the present invention. This guide catheter 10 comprises an elongate shaft 12 having a shapeable region 14 at its distal end DE and a Luer connector 15 having diametrically opposed wings 16 at its proximal end PE.

As may be appreciated from the showings of FIGS. 1A-1D, the elongate shaft 12 comprises a tubular member 22 having a helical cut 23 formed in a distal portion of the tubular member 22. This tubular member 22 may be formed of stainless steel hypotube, or any other suitable metal or plastic material. As explained more fully herein, the tubular member 22 is most flexible in the region of this helical cut 23 and, thus, the location of the helical cut 23 corresponds to the location of the shapeable region 14. A malleable shaping member 30, such as a segment of metal wire or other malleable material, is attached to the tubular member 22 in the region of the helical cut 23. An outer tubular jacket 20 is coaxially disposed outside of the tubular member 22 and an inner tubular member 24 is coaxially disposed inside of the tubular member 22. The outer tubular jacket 20 and inner tubular jacket 24 may be formed of polyurethane or other suitable plastic material and may be heat shrinkable as described below in connection with a method for manufacture of this catheter device 10. Optionally, a tubular liner 26 (e.g., thin walled polytetrafluoroethylene (PTFE) tubing may be disposed coaxially within the inner tubular jacket 24 to provide a smooth, lubricious inner luminal surface to facilitate advancement of guidewires and other devices through the inner lumen 27 of the shapeable guide catheter 10.

In operation, the user may grasp the distal end DE of the shapeable guide catheter 10 and manually bend or otherwise confirm the shapeable region 14 to a desired curvature or other shape. The malleable member 30 plastically deforms to accommodate such shaping of the shapeable regions and, thereafter, holds the shapeable region 14 in the desired curvature or other shape.

As will be explained more fully below, in some embodiments, the malleable member may be constructed and/or the width of the helical cut 23 may be varied, to provide regionalized variations in the flexibility or deformability of the shapeable region 14. Also, as described more fully below, the malleable member 30 may be more easily bendable in one plane than in another, thereby controlling the plane in which the shapeable region becomes curved. In such embodiments, the malleable member 30 may be oriented so as to be most easily bendable in a plane that is parallel to the plane of the diametrically opposed wings 16 on the proximal Luer hub. This allows the user to visually or tactilely discern the direction in which the distal portion of the catheter shaft 12 curves even when the distal portion of the catheter shaft 12 is inserted in the body of a subject.

FIGS. 2A-4C show further details of ways in which this embodiment of the shapeable guide catheter 10 may be constructed or manufactured.

Initially, as seen in FIG. 2A, a helical cut 23 is formed in a segment of stainless steel hypotube to create the tubular member 22. This helical cut 23 may be made by laser cutting or any other suitable technique. The width of the cut may be consistent over its entire length, as shown in the figures, or the cut 23 may be wider in some areas than others, thereby making the tubular member 22 more flexible in some areas than others. For manufacture of a shapeable guide catheter 10 sized for intranasal use in an adult subject, a segment of 9-11 gage stainless steel hypotube that is 10 to 25 cm in length may be used, the proximal end of the helical cut 23 may be located about 10 mm from the distal end of the hypotube and the distal end of the helical cut 23 may be located about 2 mm from the distal end of the hypotube. Although, in the embodiment shown in these drawings, a full thickness helical cut 23 is used, it will be appreciated that alternatively various other groove(s), aperture(s), cut(s) or other modifications may be made to weaken at least one region of the hypotube wall to render that region more flexible than the remainder of the hypotube.

After the helical cut has been made in the tubular member 22, the malleable shaping member 30 is welded, soldered or otherwise attached to the tubular member 22 in the region of the helical cut 23. In some embodiments, the malleable shaping member may be formed of round or flattened metal wire (e.g., annealed stainless steel wire). When a flattened wire is used, a segment of round wire may be pressed in a die as seen in FIG. 2B, or such round wire may be swaged, otherwise compressed or machined to a desired flattened shape. As indicated in FIGS. 2B' and 2B", when a round wire of diameter D is compressed, it will assume a flattened shape having a basal width B and a height H. In determining the optimal basal width B and a height H to be used, it may in some cases be desirable to determine what basal width B and a height H result in an area moment of inertia I that is equivalent to that of a round wire of a certain diameter. This may be determined, as follows:

For a round wire, the following equations apply:

$$I = \frac{\prod D^4}{64} \quad A = \frac{\prod D^2}{4} \quad D = \sqrt{\frac{4BH}{\prod}}$$

For a flattened wire, the following equations apply:

$$I = \frac{BH^3}{12} \quad A = BH \quad B = \frac{12I}{H^3}$$

Wherein,
I=Area Moment of Inertia
A=Cross Sectional Area
D=Diameter of Round Wire
B=Width of Flattened Wire
H=Height of Flattened Wire When manufacturing a shapeable guide catheter 10 suitable for intranasal use in adults, malleable shaping members 30 formed of round annealed stainless steel wire of either 0.030 inch or 0.035 inch diameter provide desirable properties (e.g., they are plastically deformable by hand but retain their shape with sufficient strength to avoid inadvertent changing of the shape as the catheter is being inserted and advanced through the intranasal anatomy.) The area moment of inertia I for such round wires are calculated to be as follows:

For 0.030 inch round wire, I=3.98E−08 in^4
For 0.035 inch round wire, I=7.37E−08 in^4

For a flattened wire to achieve an area moment of inertia I equivalent to that of either 0.030 inch 0.035 inch round wires, various other round wires having differing starting diameters may be compressed or otherwise flattened to different basal widths B and heights H, as shown in Table 1 below:

TABLE 1

| | | For I Equivalent to 0.030 in. Round Wire | | | For I Equivalent to 0.035 in. Round Wire | |
|---|---|---|---|---|---|---|
| Height (H) (in.) | Width (B) (in.) | Area Moment of Inertia (I) (in^4) | Original Wire (D) (in^4) | Width (B) (in.) | Area Moment of Inertia (I) (in^4) | Original Wire (D)(in.) |
| 0.010 | 0.477 | 3.98E−08 | 0.078 | 0.884 | 7.37E−08 | 0.106 |
| 0.011 | 0.358 | 3.98E−08 | 0.071 | 0.664 | 7.37E−08 | 0.096 |
| 0.012 | 0.276 | 3.98E−08 | 0.065 | 0.512 | 7.37E−08 | 0.088 |
| 0.013 | 0.217 | 3.98E−08 | 0.06 | 0.402 | 7.37E−08 | 0.082 |
| 0.014 | 0.174 | 3.98E−08 | 0.056 | 0.322 | 7.37E−08 | 0.076 |
| 0.015 | 0.141 | 3.98E−08 | 0.052 | 0.262 | 7.37E−08 | 0.071 |
| 0.016 | 0.116 | 3.98E−08 | 0.049 | 0.216 | 7.37E−08 | 0.066 |
| 0.017 | 0.097 | 3.98E−08 | 0.046 | 0.180 | 7.37E−08 | 0.062 |
| 0.018 | 0.082 | 3.98E−08 | 0.043 | 0.152 | 7.37E−08 | 0.059 |
| 0.019 | 0.070 | 3.98E−08 | 0.041 | 0.129 | 7.37E−08 | 0.056 |
| 0.020 | 0.060 | 3.98E−08 | 0.039 | 0.110 | 7.37E−08 | 0.053 |
| 0.021 | 0.052 | 3.98E−08 | 0.037 | 0.095 | 7.37E−08 | 0.051 |
| 0.022 | 0.045 | 3.98E−08 | 0.035 | 0.083 | 7.37E−08 | 0.048 |
| 0.023 | 0.039 | 3.98E−08 | 0.034 | 0.073 | 7.37E−08 | 0.046 |
| 0.024 | 0.035 | 3.98E−08 | 0.032 | 0.064 | 7.37E−08 | 0.044 |
| 0.025 | 0.031 | 3.98E−08 | 0.031 | 0.057 | 7.37E−08 | 0.042 |

In some embodiments, the round wire may be of tapered diameter such that the wire is largest in diameter at one end (e.g., the proximal end) and smallest in diameter at the other end (e.g., the distal end). Additionally, in some embodiments, as the wire is compressed, a transverse curvature may be created in the malleable shaping member 30 in conformity with the outer surface of the tubular member 22. Examples of these concepts are seen in FIGS. 1A-1C and 2C-2F, where the proximal end of the shaping member 30 has a height $H_1$ of 0.017 inch and a width $B_1$ of 0.070 inch, the longitudinal midpoint of the shaping member 30 has a $H_2$ of 0.010 inch and a width $B_2$ of 0.050 inch and the distal end of the shaping member 30 has a $H_3$ of 0.005 inch and a width 63 of 0.020 inch.

In the particular example shown in FIGS. 1-2G, a single malleable shaping member 30 is flattened, shaped to include a transverse curve and welded to the outer surface of the tubular member 22 in the area of the helical cut 23, as shown. However, it is to be appreciated that various other shapes and/or modes of attachment of the shaping member 30 may be employed, several non-limiting examples of such alternatives being a round wire attached to the outer surface of the tubular member 22, a flattened wire attached to the outer surface of the tubular member 22, a flattened/transversely curved wire attached to the outer surface of the tubular member 22, a flattened/transversely curved wire attached to the inner surface of the tubular member 22, or a flattened/transversely curved wire attached to the inner surface of the tubular member 22 and a second shaping member, such as a flattened/transversely curved wire, attached to the outer surface of the tubular member 22. Any permutations or combinations of these approaches, or various other approaches now specifically shown here, may be employed to provide the shapeable region 14 with the desired properties.

Figure 3A:
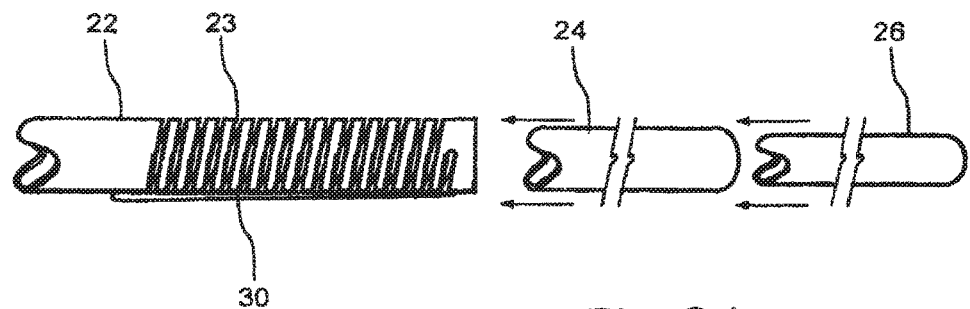
FIG. 3A shows a plastic inner tube being inserted into the lumen of the helically cut tube component after the shaping member has been attached and a plastic inner liner being inserted into the lumen of the plastic inner tube.
Figure 3B:
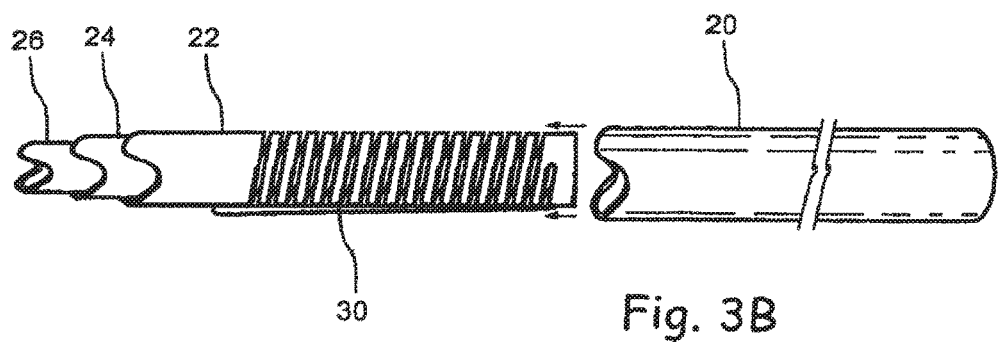
FIG. 3B shows a plastic outer jacket being advanced over the outer surface of the helically cut tube component, after the inner tube and inner liner have been inserted therein.
Figure 3C:
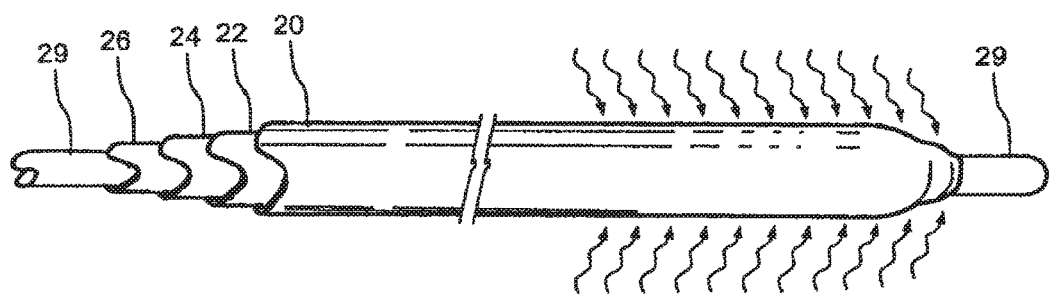
FIG. 3C shows a mandrel inserted through the lumen of the inner liner and heat being applied to heat-shrink the outer tube and to heat-fuse the outer tube, inner tube and inner liner in the region of the helical cut.

After the malleable shaping member 30 has been attached to the helically cut tubular member 22, the remainder of the guide catheter device 10 may be manufactured as shown in FIGS. 3A-3C or by any other suitable means. As seen in FIG. 3A, the tubular inner jacket 24 may be inserted into the lumen of the tubular member 22 and the optional inner liner 26 (if present) may be inserted into the lumen of the tubular inner jacket member 24. In an embodiment suitable for intranasal use in adult subjects, the tubular inner jacket 24 may comprise plastic tubing having an outer diameter of about 2.2 mm to about 3 mm and a wall thickness of about 0.1 mm to about 0.2 mm. The optional inner liner 26 may comprise a PTFE tube having an outer diameter of about 1.6 mm to about 2.8 mm and a wall thickness of about 0.05 mm.

Thereafter, as seen in FIG. 3B, the tubular outer jacket 20 may be advanced over the outer surface of the tubular member 22.

Thereafter, as seen in FIG. 3C, a mandrel 29 may be inserted through the innermost lumen of the device (e.g., through the lumen of the inner liner 26 (if present) or through the lumen of the tubular inner jacket 24 (if no inner liner is present). Heat (e.g., approximately 170 degrees C. to approximately 270 degrees C.) is then applied to heat shrink the outer jacket 20 onto the outer surface of the tubular member 22 and to cause the outer jacket 20, inner jacket 24 and inner liner 26 (if present) to heat fuse to one another through the helical cut 23. This ensures that the lumen of the device remains patent when it is shaped. In some embodiments, such as the embodiment shown in FIGS. 1 through 1D, 5 and 6, the plastic outer jacket 20, inner jacket 24 and inner liner 26 (if present) may extend distally some distance (e.g., 1 mm to 3 mm) beyond the distal end of the tubular member 22 and such protruding distal portions of these plastic components may be heat shrunk upon a reduced diameter mandrel 29, thereby providing a reduced diameter distal tip 21 on the distal end DE of the device 10. Such reduced diameter distal tip 21 may facilitate placement of the distal end DE of the device within a narrow opening or passage, such as within the ostium of a paranasal sinus.

Figure 4:
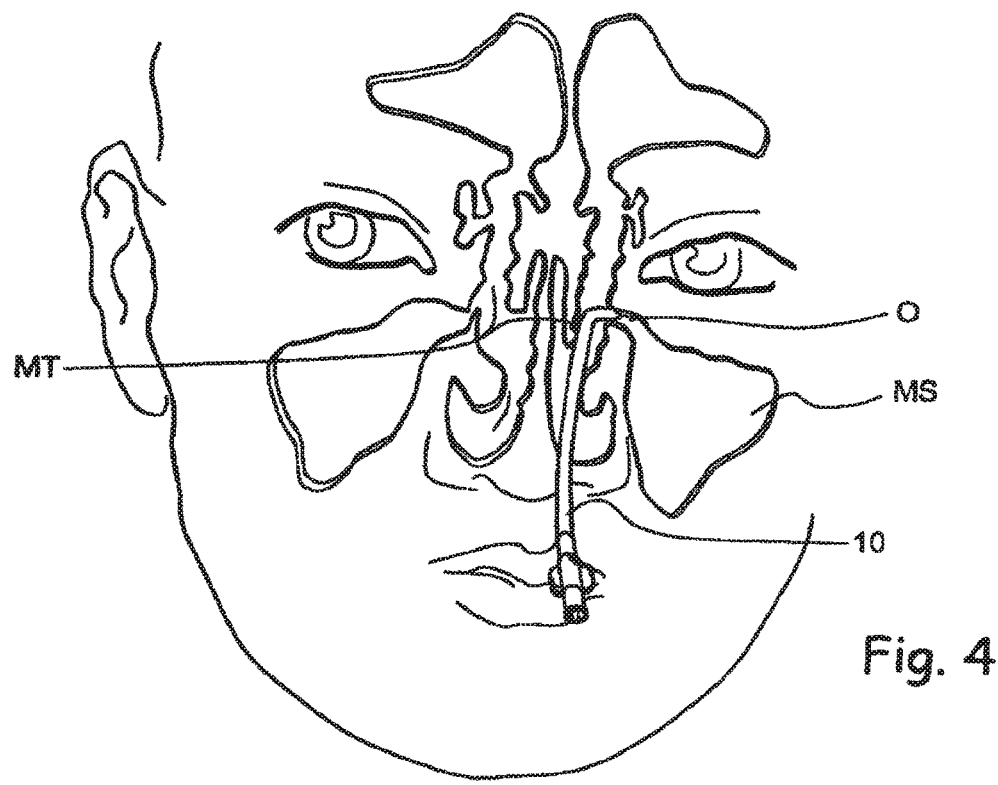
FIG. 4 is a diagram of a human patient with a malleable guide catheter of the present invention inserted trans-nasally and positioned adjacent to the ostium of the left maxillary sinus.
Figure 5:
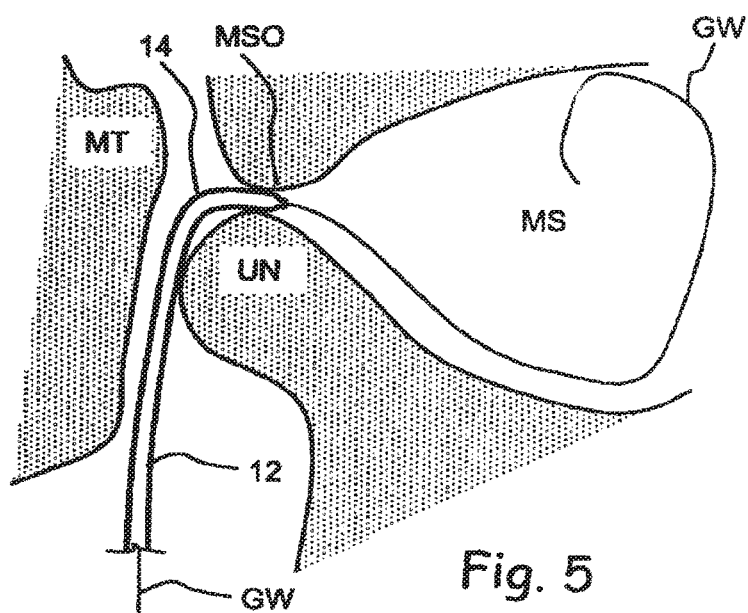
FIG. 5 is a schematic diagram showing a distal portion of a malleable guide catheter of the present invention shaped so as to extend around the intact uncinate process to a location adjacent to the ostium of the left maxillary sinus.

FIGS. 4 and 5 show examples of the manner in which a shapeable guide catheter 10 of the foregoing construction may be used to facilitate transnasal insertion of a guidewire GW into the maxillary sinus MS of a human subject. Initially, the operator may study preoperative X-rays or tomographic scans and/or may examine the anatomy around the ostium 0 of the maxillary sinus MS directly or endoscopically. After assessing the size, configuration and location of the maxillary sinus ostium MSO, as well as the surrounding anatomy, the operator will use his or her fingers (preferably while sterile) to bend the shapeable region 14 into a desired shape. Typically, the operator will select a shape that will facilitate advancement of the distal end DE of the guide catheter 10 to a position that is at or near a desired location. In this maxillary example, the "desired location" is the maxillary sinus ostium 0. Thus, to accomplish this, the operator may form the shapeable region 14 into a curve that will allows the distal end DE of the guide catheter 10 to be advanced through the middle meatus, around the uncinate process UN and into the hiatus semilunaris, resulting in placement of the reduced diameter distal tip 21 (or the distal end DE of the device 10 if no reduced diameter tip 21 is present) in front of or within the maxillary sinus ostium MSO. This will typically be done by advancing the guide catheter 10 while in a first rotational orientation to pass by the middle turbinate MT and then rotating the guide catheter 10 so as to "hook" the distal end DE around the uncinate process UN. In embodiments where the shapeable region 14 is curved in a plane that corresponds to the plane of the diametrically opposed wings 16 on the proximal Luer hub 15, the operator may feel or visualize the positioning of those wings 16 as an indicator of the current rotational orientation of the catheter 10. This will facilitate the "hooking" of the distal end DE around the intact uncinate process UN. In many procedures conducted using this guide catheter 10, the shapeable region 14 may be shaped to allow the distal end DE to reach the desired location with minimal or no surgical removal or damage to normal anatomical structures such as the uncinate process UN, middle turbinate MT or inferior turbinate. A particularly advantageous feature of the shapeable region located within about 1 cm to about 2 cm of its distal end is that the device may be inserted into the nasal cavity and then rotated and/or angled adjacent to the paranasal sinus ostia with minimal or no damage to the normal anatomical structures.

Although there may be considerable anatomical variation among subjects, a curve in the shapeable region 14 of about 90 degrees to about 110 degrees may be suitable for accessing the maxillary ostia MSO of many subjects.

After the distal end of the guide catheter 10 has been successfully placed, a guidewire GW may be advanced through the guide catheter 10 and into or through the maxillary sinus ostium MSO, as shown in FIG. 5. Thereafter, catheter(s) or other apparatus may be advanced over the guidewire GW and through the guide catheter 10 to a position within the maxillary sinus ostium MSO and/or into the cavity of the maxillary sinus MS. Alternatively, in some applications, after the guidewire GW has been successfully placed to access the desired location, the guide catheter 10 may be removed and catheter(s) or other apparatus may be advanced over the guidewire GW alone, without the use of the guide catheter 10.

If for any reason the initial shape of the shapeable region 14 is not suitable, the operator may remove the guide catheter 10 from the nose, revise the shape of the shapeable region 14, and then once again attempt insertion and successful placement of the guide catheter 10 at or near the desired location. Also, since the shapeable region 14 of this guide catheter 10 is capable of being formed into various shapes, a single guide catheter 10 may be used for accessing multiple locations, such as the ostia of different sinuses and/or other openings in the nasopharynx. Examples of the multiple locations that may be accessed using this guide catheter 10 include but are not limited to the ostia or other natural or man made openings of the frontal, maxillary, sphenoid or ethmoid sinuses, the Eustachian tubes and/or the naso-lacrimal ducts, pathological lesions, tumors, abscesses, mucocoeles, polyps, cysts, fractures, or other disease-affected tissues. To allow this diversity of applications, the shapeable region 14 may be formable into curves of many shapes, including single plane radial curves ranging from 0 degrees (i.e., straight) to about 115 degrees or higher in some applications. For example, for some applications, the curve could be 170 degrees or more.

Optionally, for some embodiments of the invention, shaping tool(s) may be used to facilitate shaping of the shapeable region 14. For example, as those of skill in the art will appreciate, one or more shaping tools (e.g., jigs, templates, fixtures, patterns, or tools similar to a pipe benders) may be used to impart specific configuration(s) to the shapeable region 14. For example, the shaping tool may comprise a jigs, template, fixture, pattern or other apparatus into or onto which the shapeable region 14 is inserted or placed and deformed (e.g., bent) to a desired configuration in conformity with that shaping tool. In some embodiments, a mandrel may be included and such mandrel may be inserted into the lumen(s) of the device during the shaping process, thereby maintaining the desired cross-sectional shape of the lumen(s) and preventing localized indentation or crimping of the lumen wall or other portions of the device. For some applications a series of shaping tools having different configurations (e.g., curves of differing severity or differing radii of curvature) may be provided separately or may be positioned on or incorporated into a common housing (e.g., a plurality of different shaping fixtures positioned on or in a common housing such as a tray or other suitable housing structure).

Figure 6A:
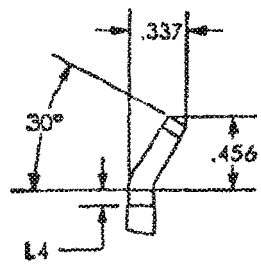
FIG. 6A shows a distal portion of a malleable guide catheter of the present invention wherein the shapeable region has been shaped to a configuration having a 30 degree curve suitable for trans-nasally accessing the ostia of a sphenoid paranasal sinuses.
Figure 6B:
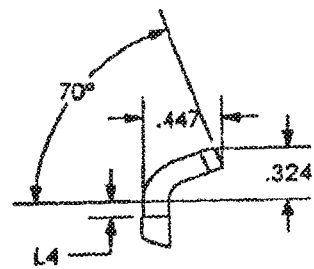
FIG. 6B shows a distal portion of a malleable guide catheter of the present invention wherein the shapeable region has been shaped to a configuration having a 70 degree curve suitable for trans-nasally accessing the ostia of a frontal paranasal sinuses.
Figure 6C:
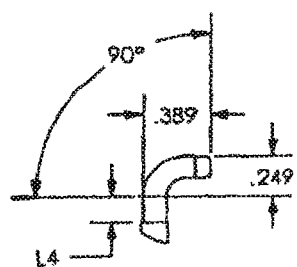
FIG. 6C shows a distal portion of a malleable guide catheter of the present invention wherein the shapeable region has been shaped to a configuration having a 90 degree curve suitable for accessing the ostia of maxillary paranasal sinus.
Figure 6D:
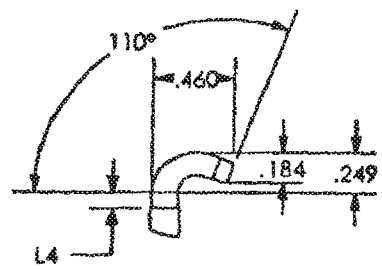
FIG. 6D shows a distal portion of a malleable guide catheter of the present invention wherein the shapeable region has been shaped to a configuration having a 110 degree curve suitable for accessing the ostia of a maxillary paranasal sinuses.

Irrespective of whether the shaping of the shapeable region 14 is carried out by hand or with the use of shaping tool(s), it may be desirable for the shapeable region 14 to be alternately configurable in shapes that are the same or substantially similar to those of the paranasal sinus guide catheters described in Parent application Ser. No. 11/150, 847, now U.S. Pat. No. 7,803,150, which is expressly incorporated herein by reference. FIGS. 6A-6D of this application show several specific shapes that may be imparted to the shapeable region 14 to facilitate advancement and positioning of the distal end of the guide catheter device within or adjacent to/in alignment with the ostia of different paranasal sinuses. These specific shapes have curves of 30 degrees (FIG. 6A), 70 degrees (FIG. 6B), 90 degrees (FIG. 6C) and 110 degrees (FIG. 6D). The configuration having the 30 degree curve is typically useable for accessing the ostia of sphenoid sinuses or in some cases a 0 degree distal end shape is used for sphenoid sinuses. The configuration having the 70 degree curve is typically useable for accessing the ostia of frontal sinuses. The configuration having the 90 degree curve is typically useable for accessing the ostia of maxillary sinuses and in some cases frontal sinuses. The configuration having the 110 degree curve is typically useable for accessing the ostia of maxillary sinuses without requiring surgical removal or mitigation of the uncinate process. Each of these configurations shown in FIGS. 6A-6D have a transverse dimension or envelope that is small enough to allow the distal end of the guide catheter device to be inserted transnasally and advanced to the desired sinus ostium without requiring removal or surgical alteration of existing, normal anatomical structures within the nose.

Figure 7:
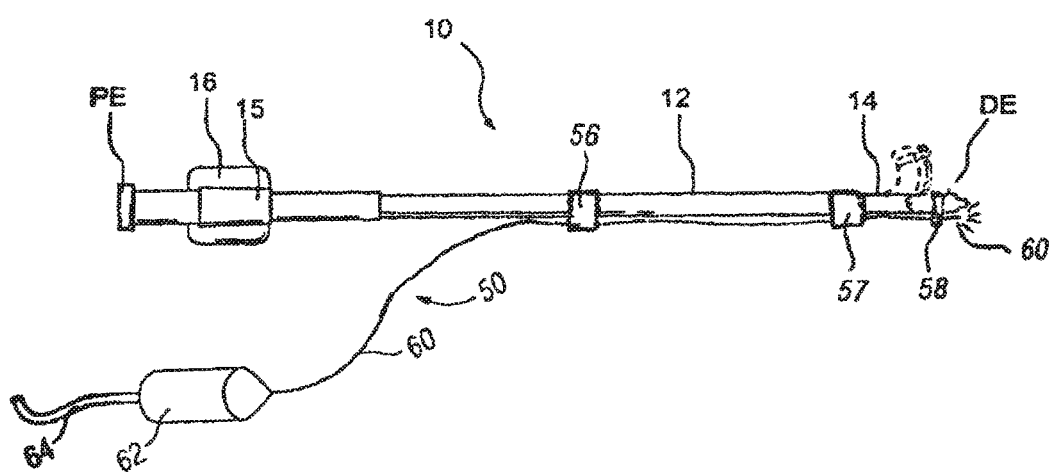
FIG. 7 is a side view of a malleable guide catheter of the present invention with an optional endoscopic system.

FIG. 7 shows the above-described guide catheter device 10 with an optional flexible endoscope system 50 that may be attached to or integrated with any guide catheter of this invention such that the guide catheter device may be used in conjunction with the endoscope system 50. This endoscope system 50 comprises a flexible endoscope 60, such as a fiber optic scope, that is attached to the shaft 12b of the guide catheter device 10b by way of connectors 56, 57, 58 such as clips, bands, snap-in grooves, etc. In some embodiments, the connectors 56, 57, 58 may be constructed to allow the endoscope 60 to be longitudinally advanced and retracted relative to the shaft of the guide catheter 10. The endoscope 60 is connected to a camera 62 and the camera 62 is connectable by way of camera cable 64 to a monitor on which an image received through the endoscope 60 may be displayed. Each endoscope 60 has a particular field of view. In this system, the vantage point of the endoscope 60 may be changed by changing the configuration of the shapeable region 14, thus bringing different anatomical structures and/or anatomical areas within the endoscope's field of view. Also, in embodiments where the endoscope 60 is advanceable, the degree of curvature of the shapeable region 14 may be changed to guide the advancement of the endoscope as desired. For example, if it is desired to cause the endoscope to advance through—the ostium of a paranasal sinus and into the sinus cavity, the operator may position the distal end DE of the guide catheter 10 near the ostium, visualize the ostium with the scope, and then guide the endoscope 60 into the ostium as desired. Also, in some applications, such as when it is desired to pass a guidewire or other device through the frontal outflow tract and into a frontal sinus, the operator may be faced with confusing anatomy, such as the presence of one or more false or blind openings in addition to the actual opening through which the guidewire or device is intended to pass. In such instances, the optional endoscope 60 may be used to assist the operator in serially or systematically probing or identifying each available opening, thereby facilitating identification of the correct opening and simplifying passage of the guidewire or device into the correct passage. Examples of endoscopes that may be used in this system include those described in U.S. patent application Ser. No. 11/803,695, entitled "Endoscopic Methods And Devices For Transnasal Procedures," filed May 14, 2007, now U.S. Pat. No. 9,554,691; U.S. patent application Ser. No. 11/647,530, entitled "Endoscopic Methods and Devices for Transnasal Procedures," filed Dec. 27, 2006, published as U.S. Pub. No. 2007/0167682, now abandoned; U.S. patent application Ser. No. 11/725,151, entitled "Endoscopic Methods and Devices for Transnasal Procedures," filed Mar. 15, 2007, now U.S. Pat. No. 9,089,258; and U.S. Provisional Patent Application No. 60/844,874, entitled "Endoscopic Methods and Devices for Transnasal Procedures," filed Sep. 15, 2006.

The invention has been described hereabove with reference to certain examples or embodiments of the invention only. Various additions, deletions, alterations and modifications may be made to these examples and embodiments without departing from the intended spirit and scope of the invention. For example, any element or attribute of one embodiment or example may be incorporated into or used with another embodiment or example, unless otherwise indicated or unless doing so would render the embodiment or example unsuitable for its intended use. Also, where the steps of a method or procedure are referred to or listed in a specific order, the order of such steps may be changed unless otherwise specified or unless doing so would render the method or procedure unsuitable for its intended use. All reasonable additions, deletions, modifications and alterations are to be considered equivalents of the described examples and embodiments and are to be included within the scope of the following claims.

What is claimed is:

1. An apparatus comprising:
   (a) a guide member, wherein the guide member comprises a shaft having a shapeable region, wherein the shapeable region is configured to bend from a first bend angle to a second bend angle, wherein the shapeable region is configured to fit in a nasal cavity of a patient;
   (b) a shaping member extending and secured along a corresponding length of the shapeable region, wherein the shaping member is malleable, wherein that the shaping member is coupled with the shapeable region of the guide member such that the shaping member is configured to bend from a first corresponding bend angle to a second corresponding bend angle in order to deform the shapeable region of the guide member from the first bend angle to the second bend angle, respectively; and
   (c) a dilation catheter slidably coupled with the guide member, wherein the dilation catheter comprises an inflatable balloon, wherein the inflatable balloon is sized and configured to dilate a drainage passageway associated with a paranasal sinus.

2. The apparatus of claim 1, wherein the shapeable region includes a cut region of the shaft.

3. The apparatus of claim 2, wherein the cut region includes a helical cut.

4. The apparatus of claim 1, wherein the guide member comprises a stainless steel hypotube.

5. The apparatus of claim 1, wherein the guide member comprises a plastic material.

6. The apparatus of claim 1, wherein the guide member comprises a catheter.

7. The apparatus of claim 1, wherein the shaping member comprises a metallic wire.

8. The apparatus of claim 1, further comprising an outer tubular jacket coaxially disposed about the shaft of the guide member.

9. The apparatus of claim 7, wherein the outer tubular jacket comprises a plastic material.

10. The apparatus of claim 1, further comprising an inner liner disposed within the shaft.

11. The apparatus of claim 9, wherein the inner liner comprises polytetrafluoroethylene.

12. The apparatus of claim 1, wherein the shaping member comprises at least two wires.

13. The apparatus of claim 1, further comprising a guidewire slidably disposed in the guide member.

14. The apparatus of claim 13, wherein the dilation catheter is slidably disposed over the guidewire.

15. The apparatus of claim 1, wherein the shapeable region is configured to bend to a bend angle up to 110 degrees.

16. The apparatus of claim 1, further comprising an endoscope attached to the guide member.

17. An apparatus comprising:
    (a) a guide member, wherein the guide member comprises a shaft defining a longitudinal axis, wherein the shaft includes:
       (i) a proximal end,
       (ii) a distal end, wherein the distal end is configured to fit within a nasal cavity in a patient, and
       (iii) a flexible region near the distal end, wherein the distal end includes one or more cuts configured to provide flexibility to the flexible region;
    (b) a metallic wire comprising a proximal portion secured to the flexible region of the shaft, wherein the metallic wire is operable to selectively bend with the flexible region from a first bend angle to a second bend angle while the metallic wire is secured to the flexible region of the shaft to thereby deflect the distal end relative to the longitudinal axis, wherein the metallic wire and the flexible region are configured to cooperate to maintain a bend in the flexible region; and
    (c) a dilation catheter slidably coupled with the guide member, wherein the dilation catheter comprises an inflatable balloon, wherein the inflatable balloon is sized and configured to dilate a drainage passageway associated with a paranasal sinus.

18. The apparatus of claim 17, wherein the shaft is formed of a metallic material.

19. An apparatus comprising:
(a) a guide member, wherein the guide member comprises a shaft having a shapeable region, wherein the shapeable region is operable to bend from a first bend angle to a second bend angle, wherein the shapeable region is configured to fit in a nasal cavity of a patient;
(b) a shaping member terminating at a proximal portion, wherein the proximal portion is fixed to a corresponding portion of the shaft, wherein the shaping member is attached to the shapeable region of the guide member, wherein the shaping member is operable to deform from a first corresponding bend angle to a second corresponding bend angle in order to bend the shapeable region from the first bend angle to the second bend angle, respectively; and
(c) a dilation catheter slidably coupled with the guide member, wherein the dilation catheter comprises an inflatable balloon, wherein the inflatable balloon is sized and configured to dilate a drainage passageway associated with a paranasal sinus.

* * * * *